United States Patent

Reers

[11] Patent Number: 5,563,041
[45] Date of Patent: Oct. 8, 1996

[54] METHOD FOR DETERMINING PLATELET AGGREGATION

[75] Inventor: Martin Reers, Marburg-Michelbach, Germany

[73] Assignee: Behringwerke Aktiengesellschaft, D-35001 Marburg-Michelbach, Germany

[21] Appl. No.: 365,759

[22] Filed: Dec. 29, 1994

[30] Foreign Application Priority Data

Dec. 30, 1993 [DE] Germany .................. 43 44 919.0

[51] Int. Cl.$^6$ .............. C12Q 1/56; C12Q 1/00; C12N 9/48; A61K 35/14
[52] U.S. Cl. ................ 435/13; 435/4; 435/183; 435/212; 530/380; 530/381; 530/382; 530/829; 530/830
[58] Field of Search .................. 435/13, 4, 183, 435/212; 530/829, 830, 380, 381, 382

[56] References Cited

FOREIGN PATENT DOCUMENTS

0513543A1  11/1992  European Pat. Off. .

OTHER PUBLICATIONS

Michelson "Platelet Activation by Thrombin Can Be Directly Measured in Whole Blood Through Use of The Peptide GPRP & Flow Cytometry" Blood Coagul. Fibrinolys. 5121–131 1994.

Kawasaki et al "Amino Acids & Peptides XVI Synthesis of N–Terminal Tetrapeptide Analogs of Fibrin α–Chain" Chem Pharm Bull 40(12) 3253–3260 1992.

Circ Res. Adelman et al "Synergistic Inhibition of Platelet Aggregation by Fibrinogen Related Peptides" 67(4) 941–947 1990.

S. C. T. Lam et al., *Rapid Dissociation of Platelet–Rich Fibrin Clots in Vitro By A Combination of Plasminogen Activators and Antiplatelet Agents*, The Journal of Pharmacology & Experimental Therapeutics, 259: 1371–1378, 1991.

A. P. Laudano et al., *Synthetic Peptide Derivatives that Bind To Fibrinogen and Prevent the Polymerization of Fibrin Monomers*, Proc. Natl. Acad. Sci. U.S.A. 75: 3085–3089, 1978.

*Primary Examiner*—Mindy Fleisher
*Assistant Examiner*—Nancy J. Degen
*Attorney, Agent, or Firm*—Finnegan, Henderson, Farabow, Garrett & Dunner, L.L.P.

[57] ABSTRACT

The invention relates to a method for determining platelet aggregation in the presence of an inhibitor of fibrin aggregation, which prevents the formation of an interfering fibrin clot, and to a diagnostic aid for determining the platelet aggregation-inhibiting action of thrombin inhibitors.

11 Claims, 1 Drawing Sheet

Thrombin-induced platelet aggregation in the presence of fibrin aggregation inhibitor in PRP

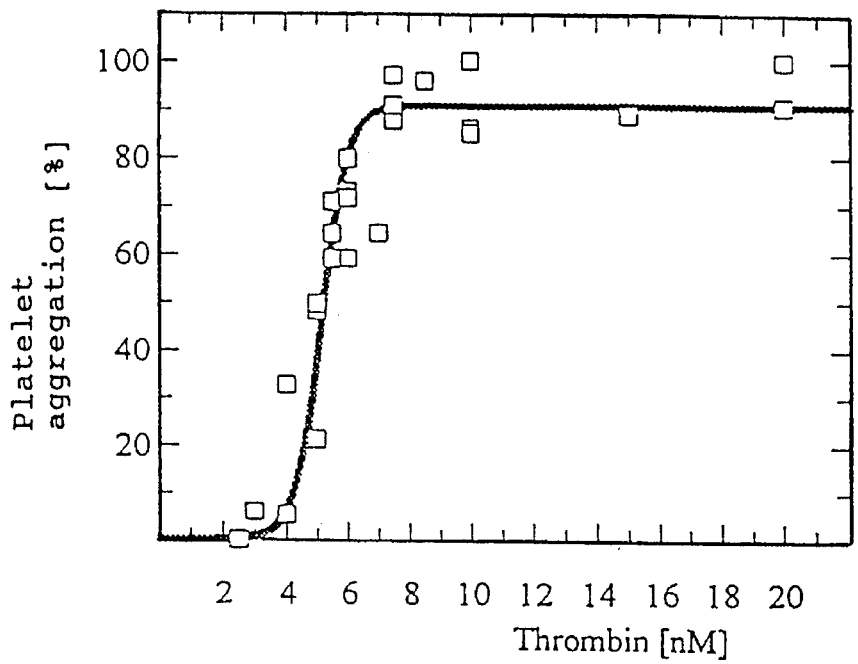
Fig. 1  Thrombin-induced platelet aggregation in the presence of fibrin aggregation inhibitor in PRP
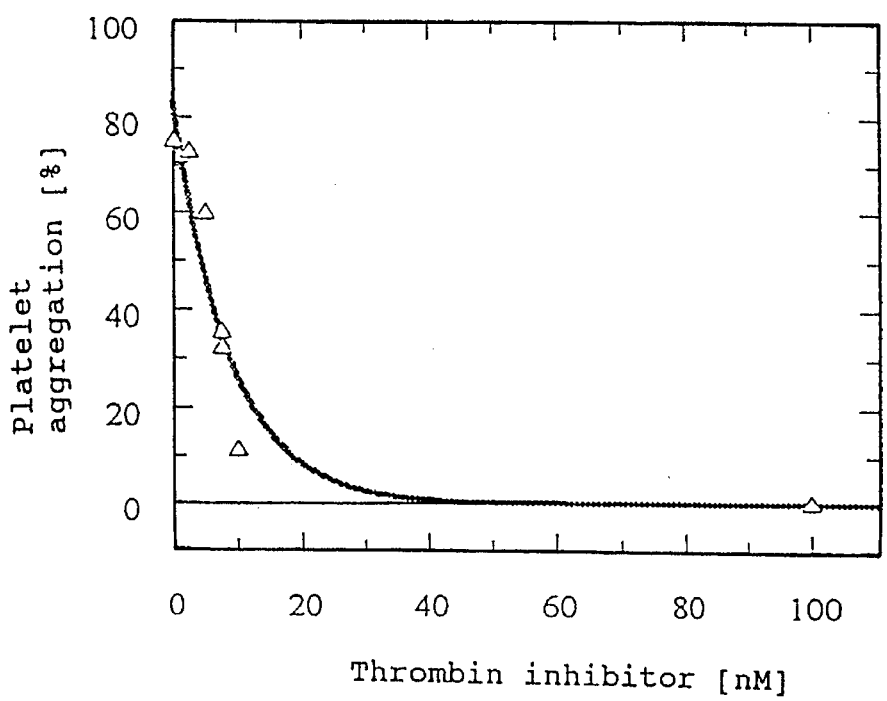
Fig. 2  Determination of the efficiency ($IC_{50}$) of a thrombin inhibitor on platelet aggregation in PRP

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Gly Pro Arg
1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Gly Pro Arg Pro
    1

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is amide."

( x i ) SEQUENCE DESCRIPTION: SEQ ID NO:3:

Gly Pro Arg Pro Ala Xaa
    1                 5

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="Xaa is sarcosine."

( x i ) SEQUENCE DESCRIPTION: SEQ ID NO:4:

Gly Pro Arg Xaa
    1

METHOD FOR DETERMINING PLATELET AGGREGATION

The invention relates to a method for determining platelet aggregation in the presence of an inhibitor of fibrin aggregation, which prevents the formation of an interfering fibrin clot, and to a diagnostic aid for determining the platelet aggregation-inhibiting action of thrombin inhibitors.

It is possible to use for determining the platelet aggregation-inhibiting action of thrombin inhibitors for example diagnostic systems which contain a platelet suspension such as platelet-rich plasma (PRP) and thrombin, with the thrombin initiating aggregation of the platelets. The rate or the extent of the aggregation can be determined by a turbidity measurement, for example by turbidimetry or nephelometry. On addition of thrombin inhibitors, platelet aggregation is slowed down as a function of the amount added, so that quantification of the inhibitory effect is possible from the turbidity measurement.

In the case of, for example, thrombin-induced platelet aggregation in platelet-rich plasma (PRP), a thrombin-induced fibrin clot gives rise to difficulties with the measurement technique. In the prior art methods it is possible to use only very low concentrations of thrombin so that maximum platelet aggregation cannot be reached. However, even with low thrombin concentrations interfering fibrin clots are produced after a certain time. In order nevertheless to be able to use higher concentrations of thrombin leading to a better detection signal it is necessary to carry out an elaborate platelet washing process.

The object of the present invention was therefore to provide a method which makes it possible to determine experimentally induced platelet aggregation and to determine thrombin inhibitors without the interfering effect of a fibrin clot.

It is known that short peptides starting with the sequence Gly-Pro-Arg SEQ ID NO: 1 bind to fibrinogen (Proc. Natl. Acad. Sci U.S.A., 1978, 75, 3085-3089). Furthermore, the peptide Gly-Pro-Arg-Pro SEQ ID NO: 2 has been used in combination with antiplatelet reagents in platelet disaggregation experiments (Pharmacology and Experimental Therapeutics, 1991, 259, 1371-1378). It is additionally known that Gly-Pro-Arg-Pro-Ala Xaa -$NH_2$ SEQ ID NO: 3 can be used as fibrin aggregation Inhibitor in methods for determining F XIIIa and fibrinogen.

It has now been found, surprisingly, that the formation of an interfering fibrin clot is suppressed by adding an inhibitor of fibrin aggregation, even at high thrombin concentrations and without affecting the experimentally required platelet aggregation.

The present invention thus relates to a method for qualitative or quantitative determination of the platelet aggregation induced by thrombin, which comprises preventing the formation of an interfering fibrin clot by the presence of an inhibitor of fibrin aggregation.

BRIEF DESCRIPTION OF THE DRAWINGS

FIG. 1 shows the thrombin-induced platelet aggregation (ratio of aggregated to non-aggregated platelets in %) in PRP as a function of the concentration of thrombin in nM in the presence of a fibrin aggregation inhibitor.

FIG. 2 shows the determination of the efficiency ($IC_{50}$) of a thrombin inhibitor on platelet aggregation in PRP.

Suitable inhibitors of fibrin aggregation are peptides or peptide derivatives, especially those-having a structure analogous to the amino-terminal end of the human fibrin chain. Such inhibitors of fibrin aggregation are described, for example, in A.P. Laudano et al. (1978) Proc. Natl. Acad. Sci. U.S.A., 75, 3085-3089. Preferred peptides are those which contain the sequence Gly-Pro-Arg SEQ ID NO: 1 or Gly-Pro-Arg-Pro SEQ ID NO: 2.

The peptide or peptide derivative with the sequence Gly-Pro-Arg SEQ ID NO: 1, Gly-Pro-Arg-Pro SEQ ID NO. 2 or Gly-Pro-Arg-Xaa SEQ ID NO: 4 is particularly preferred.

Especially preferred furthermore is Gly-Pro-Arg-Pro-Ala-Xaa $NH_2$ SEQ ID NO: 3.

The invention furthermore relates to the use of the method described above for determining the platelet aggregation-inhibiting action of platelet inhibitors, wherein the thrombin inhibitor to be determined and the inhibitor of fibrin aggregation are present simultaneously in the assay mixture. Surprisingly, it is possible with this method not only to detect but also to quantify thrombin inhibitors present, for example, in plasma. However, qualitative or quantitative detection is also possible using the method according to the invention in liquids other than plasma.

The invention furthermore relates to a diagnostic aid containing thrombin and an inhibitor of fibrin aggregation. A diagnostic aid of this type is suitable for carrying out the method according to the invention for the qualitative or quantitative determination of the platelet aggregation-inhibiting action of thrombin inhibitors in liquids, for example in plasma.

A method for determining inhibitors of platelet aggregation, for example in a buffer solution or in patients' samples, is described by way of example hereinafter. The assay can be carried out in the following steps:

introduction of platelet-rich plasma (PRP)

addition of citrate solution or platelet-poor plasma (PPP)

addition of the fibrin aggregation inhibitor which is, where appropriate, dissolved in a buffer solution addition of the sample to be tested; the inhibitor to be detected can, for example, be dissolved in a buffer solution or in PPP or be present in plasma; various concentration levels (serial dilution) are assayed incubation at about 37° C. for a period of 1 to 20 minutes addition of an inducer of platelet aggregation, for example thrombin measurement of the platelet aggregation.

This determination requires only small volumes: PRP preferably 300 µl; solution of the fibrin aggregation inhibitor preferably 25 µl thrombin inhibitor solution, for example CRC $2^{20}$ (4-methoxy-2,3,6-trimethylphenyl- sulfonyl-L-aspartyl-D-4-amidinophenyl-alanylpiperidide EP 0 513 543) or PPP, preferably 25 µl. The total volume is 300–1000 µl, preferably 500 µl. In order to obtain a defined volume of, for example, 500 µl it is possible to add a solution which is composed of a 0.38% strength citrate solution which has been diluted 10-fold with isotonic NaCl solution. The measurement of platelet aggregation is preferably carried out in a 1 ml cuvette in an aggregometer such as, for example, an APACT (Automated Platelet Aggregation and Coagulation Tracer) from LAbor (Laborgerate und Analysesysteme Vertriebsgesell-schaft mbH, Ewige Weide 7, D-22926 Ahrensburg, Germany) at 37° C. with stirring.

PRP can be prepared in a citrate solution in a known manner. The platelet count ranges between $10^7$ and $10^9$ per ml, preferably $2 \times 10^8$ per ml. The platelet concentration for optimal aggregation can be determined with the aid of a conventional platelet agonist, for example collagen, ADP or thromboxane $A_2$.

The concentration of the fibrin aggregation inhibitor is in the range 1–20 mM, preferably 10 mM. The thrombin concentration range is preferably 4–7 nM, corresponding to about 80% of the maximum platelet aggregation which can be achieved with thrombin.

Abbreviations:

| | |
|---|---|
| PRP | platelet-rich plasma |
| PPP | platelet-poor plasma |
| Gly | glycine |
| Pro | L-proline |
| Arg | L-arginine |
| Ala | L-alanine |
| Sar | Sarcosine |
| $NH_2$ | amide |
| mM | millimole/liter |
| nM | nanomole/liter |

The following examples 11illustrate the invention in detail:

EXAMPLE 1

Determination of Platelet Aggregation

FIG. 1 shows the thrombin-induced platelet aggregation (ratio of aggregated to non-aggregated platelets in %) in PRP as a function of the concentration of thrombin in nM in the presence of a fibrin aggregation inhibitor. This makes it possible to use a distinctly higher thrombin concentration than in the prior art. A reference plot which is expanded in this way makes a considerable contribution to the precise determination of platelet aggregation.

As is evident from FIG. 1, the platelet aggregation increases linearly, over the range of about 10–80% of the maximum platelet aggregation achievable, with the added thrombin concentration of 4–7 nM (0.4–0.7 IU/ml).

EXAMPLE 2

Preparation of Solution A (Citrate Solution)

The following substance is dissolved in 100 ml of water: 380 mg of trisodium citrate dihydrate. The solution may, where appropriate, also contain 500 mg of D-(+)-glucose and 350 mg of albumin.

Preparation of Solution B (PRP)

90 ml of fresh whole blood from donors are introduced into a polyethylene vessel which already contains 10 ml of a 3.8% strength (w/v) trisodium citrate dihydrate solution. This anticoagulated blood is immediately centrifuged at 200 g for 20 min. The supernatant is transferred into a new polyethylene vessel and stored at 0° C. until used.

Preparation of Solution C (Fibrin Aggregation Inhibitor)

The following substances are dissolved in 100 ml of water: 1 g of bovine serum albumin and 10 g of Gly-Pro-Arg-Pro-Ala-Xaa-$NH_2$ SEQ ID NO: 3. The solution is stored at −20° C. until used.

Preparation of Solution D (Thrombin Inhibitor)

The following substance is dissolved in 100 ml of water: 127.6 mg of thrombin inhibitor CRC 220 (4-methoxy-2,3,6-trimethylphenylsulfonyl-L-aspartyl-D-4-amidinophenylalanylpiperidide). CRC 220 solutions diluted with isotonic saline solution are prepared for use in the assay. All the solutions are made up freshly and cooled to 0° C.

Preparation of Solution E (Thrombin)

4.2 µg of human α-thrombin are dissolved in 1 ml of water (10 IU/ml). Thrombin solutions diluted with isotonic saline solution are prepared for use in the assay. All the solutions are made up freshly and cooled to 0° C.

Assay Procedure

300 µl of solution B, 100 µl of solution A, 25 µl of solution C and 25 µl of solution D are pipetted into a measuring cuvette with a capacity of 1 ml (1 cm path length, continuous stirring) of the APACT aggregometer (LAbor) and preincubated at 37° C. for 1 min. Then 50 µl of solution E are added and the light transmission is recorded as a function of time. Measurement is continued until the signal is constant, which is usually reached after 5 minutes. Increasing concentrations of thrombin inhibitor are added to each assay mixture. Knowing the added amounts of thrombin inhibitor it is possible to determine quantitatively, for example, an $IC_{50}$ for the thrombin inhibitor (FIG. 2). The $IC_{50}$ for this example is found to be 10 nM.

I claim:

1. A method for the qualitative or quantitative determination of platelet aggregation induced by thrombin in the presence of fibrin, wherein the formation of an interfering fibrin clot is prevented by the presence of an inhibitor of fibrin aggregation and the experimentally induced platelet aggregation is unaffected.

2. The method as claimed in claim 1, wherein the inhibitor of fibrin aggregation is a peptide or peptide derivative.

3. The method as claimed in claim 2, wherein the peptide or peptide derivative contains at its aminoterminal end a structure analogous to the aminoterminal end of the human αfibrin chain.

4. The method as claimed in claim 3, wherein the structure is a peptide having the sequence Gly-Pro-Arg (SEQ ID NO:1) or Gly-Pro-Arg-Pro (SEQ ID NO:2).

5. (Amended) The method as claimed in claim 2, wherein the peptide or peptide derivative has the sequence Gly-Pro-Arg (SEQ ID NO:1), Gly-Pro-Arg-Pro (SEQ ID NO:2), Gly-Pro-Arg-Xaa (SEQ ID NO:4) or Gly-Pro-Arg-Pro-Ala-Xaa-NH$_2$ (SEQ ID NO:3).

6. The method as claimed in claim 1, wherein 4 to 7 nM thrombin is employed.

7. A method for the qualitative or quantitative determination of the platelet aggregation-inhibiting action of a thrombin inhibitor, comprising performing the method of claim 1 in the presence of said thrombin inhibitor.

8. A diagnostic aid for determining the platelet aggregation-inhibiting action of thrombin inhibitors containing thrombin an inhibitor of fibrin aggregation and platelets.

9. A diagnostic aid for determining the platelet aggregation-inhibiting action of thrombin inhibitors containing thrombin, an inhibitor of fibrin aggregation and platelet rich plasma.

10. A diagnostic aid for determining the platelet aggregation-inhibiting action of thrombin inhibitors containing thrombin, an inhibitor of fibrin aggregation and a polyethylene vessel for preparing platelet rich plasma.

11. A diagnostic aid for determining the platelet aggregation-inhibiting action of thrombin inhibitors containing thrombin and Gly-Pro-Arg-Pro-Ala-Xaa-NH$_2$ (SEQ ID NO:3) as an inhibitor of fibrin aggregation.

* * * * *

UNITED STATES PATENT AND TRADEMARK OFFICE
CERTIFICATE OF CORRECTION

PATENT NO. : 5,563,041
DATED : October 08, 1996
INVENTOR(S) : Martin REERS

It is certified that error appears in the above-indentified patent and that said Letters Patent is hereby corrected as shown below:

Title Page, Assignee, line 2, "Marburg-Michelbach" should read --Marburg--.

Claim 3, Column 5, line 61, "αfibrin" should read --α fibrin--.

Claim 5, Column 5, line 65, delete "(Amended)".

Claim 8, Column 6, line 59, after "thrombin", insert --,--.

Signed and Sealed this

Fifteenth Day of April, 1997

Attest:

BRUCE LEHMAN

Attesting Officer  Commissioner of Patents and Trademarks